United States Patent
King

(10) Patent No.: US 9,498,323 B2
(45) Date of Patent: Nov. 22, 2016

(54) STENT GRAFT HAVING MOVABLE FENESTRATED TUBULAR BRIDGE

(71) Applicant: Cook Medical Technologies LLC, Bloomington, IN (US)

(72) Inventor: Chantelle King, Woodridge (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/848,895

(22) Filed: Sep. 9, 2015

(65) Prior Publication Data

US 2016/0067033 A1    Mar. 10, 2016

(30) Foreign Application Priority Data

Sep. 10, 2014    (AU) .................... 2014221326

(51) Int. Cl.
| | |
|---|---|
| *A61F 2/06* | (2013.01) |
| *A61F 2/07* | (2013.01) |
| *A61F 2/844* | (2013.01) |
| *A61F 2/86* | (2013.01) |
| *A61F 2/82* | (2013.01) |

(52) U.S. Cl.
CPC ................ *A61F 2/07* (2013.01); *A61F 2/844* (2013.01); *A61F 2/86* (2013.01); *A61F 2002/061* (2013.01); *A61F 2002/072* (2013.01); *A61F 2002/825* (2013.01); *A61F 2230/0034* (2013.01); *A61F 2230/0069* (2013.01)

(58) Field of Classification Search
CPC .......... A61F 2/07; A61F 2/856; A61F 2/954; A61F 2002/075; A61F 2002/061
See application file for complete search history.

(56) References Cited

U.S. PATENT DOCUMENTS

| | | | |
|---|---|---|---|
| 6,395,018 B1 | 5/2002 | Castaneda | |
| 6,478,817 B2 * | 11/2002 | Schmitt | ............ A61F 2/06 623/1.35 |
| 8,167,926 B2 | 5/2012 | Hartley et al. | |
| 8,702,786 B2 | 4/2014 | Roeder et al. | |
| 2006/0074484 A1 | 4/2006 | Huber | |
| 2007/0219621 A1 * | 9/2007 | Hartley | ............ A61F 2/07 623/1.13 |
| 2008/0228260 A1 | 9/2008 | Hannay | |
| 2009/0043377 A1 * | 2/2009 | Greenberg | ............ A61F 2/07 623/1.35 |

(Continued)

FOREIGN PATENT DOCUMENTS

| | | |
|---|---|---|
| WO | 2004064686 A1 | 8/2004 |
| WO | 2011070576 A1 | 6/2011 |

OTHER PUBLICATIONS

European Search Report, Application No. 15275146.7, Applicant Cook Medical Technologies LLC, Jan. 19, 2016.

*Primary Examiner* — Thomas J Sweet
*Assistant Examiner* — Tiffany Shipmon
(74) *Attorney, Agent, or Firm* — Richard J. Godlewski

(57) ABSTRACT

A stent graft comprising an elongate main tubular body of a biocompatible graft material is disclosed. The main tubular body comprises a main lumen, a distal end and a proximal end; and an elongate tubular bridge of a biocompatible graft material. The elongate tubular bridge extends around a portion of the main tubular body so as to form a bridging lumen bridging between two circumferentially spaced-apart openings within the main tubular body. The tubular bridge has at least two fenestrations. The tubular bridge comprises concertinaed graft material.

21 Claims, 4 Drawing Sheets

(56) References Cited

U.S. PATENT DOCUMENTS

2012/0035714 A1* 2/2012 Ducke .................. A61F 2/07
 623/1.34
2012/0130478 A1 5/2012 Shaw
2013/0013051 A1* 1/2013 Benary .................. A61F 2/07
 623/1.13
2014/0100650 A1 4/2014 Chobotov

* cited by examiner

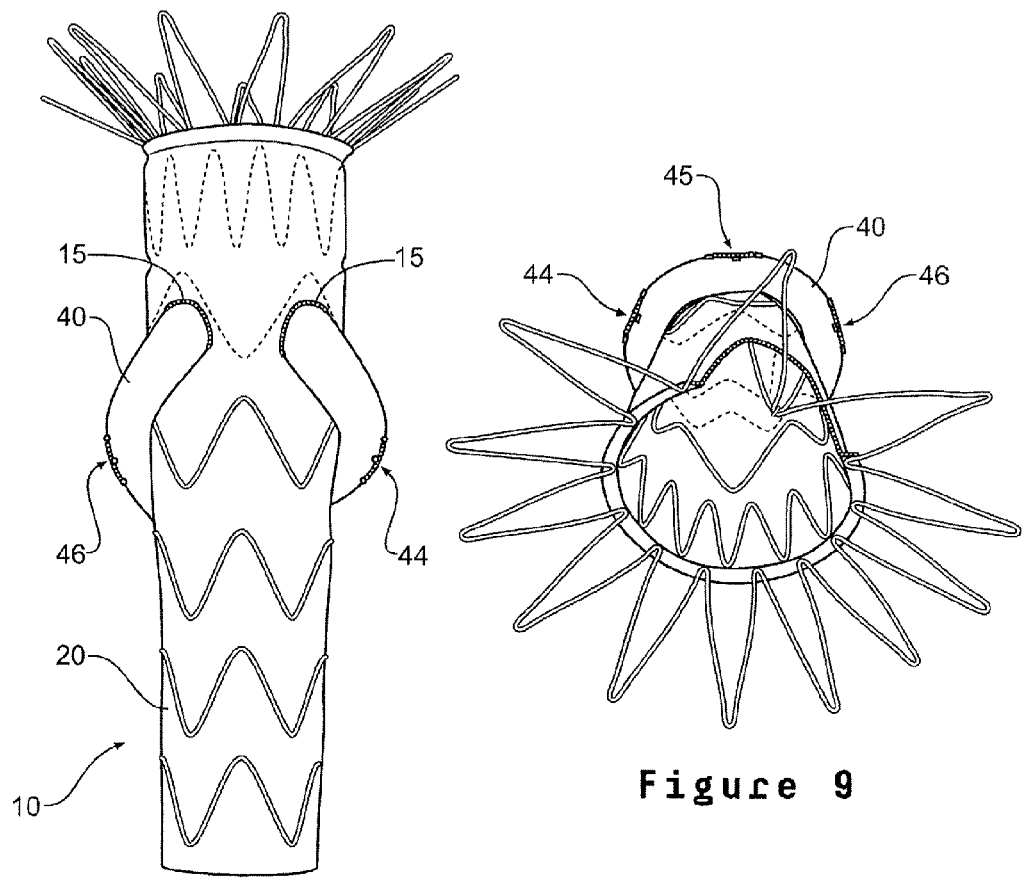
Figure 8
Figure 9
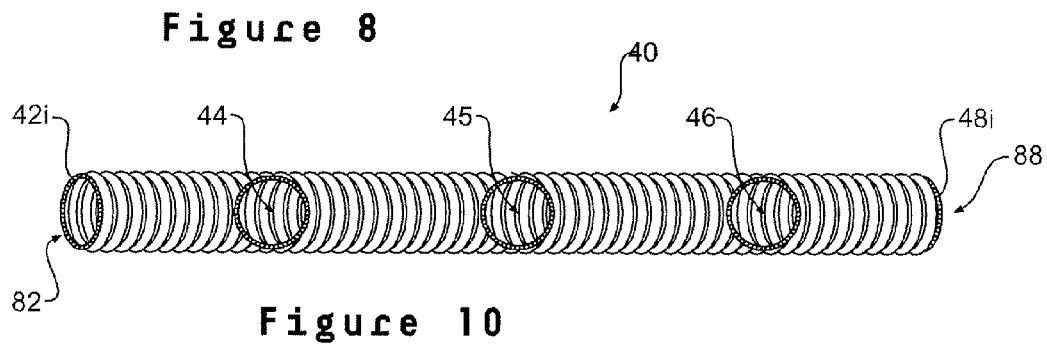
Figure 10
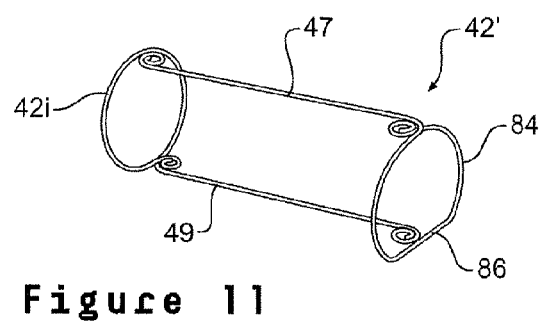
Figure 11

STENT GRAFT HAVING MOVABLE FENESTRATED TUBULAR BRIDGE

FIELD OF THE INVENTION

The present invention relates to a medical device and more particularly to a medical device for endovascular deployment into the aorta of a patient.

BACKGROUND

The present invention relates to a stent graft for endovascular deployment into the aorta of a patient to treat arterial disease such as an aneurism. An aortic aneurysm can extend to the para-renal or supra-renal region of the descending aorta. To obtain good proximal seal, it may be necessary to deploy a stent graft which could potentially cover one or more of the branch vessels of the descending aorta in that region.

In the descending aorta there are a number of branch vessels which it is important not to occlude during the placement of a stent graft into the descending aorta to span an aneurism or the like. These vessels include the superior mesenteric artery, the celiac artery and the renal arteries.

The relative position of these arteries can vary considerably from patient to patient and hence it has often been necessary to manufacture a custom made device to fit a particular vasculature.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels, similar terms such as caudal and cranial should be understood.

Throughout this discussion the term "stent graft" is intended to mean a device which has a tubular body of bio-compatible graft material and at least one stent fastened to the tubular body to define a lumen through the stent graft. The stent graft may be bifurcated and have fenestrations, side arms or the like. Other arrangements of stent grafts are also within the scope of the disclosure.

SUMMARY

According to a first aspect of the invention, there is provided a stent graft comprising:
an elongate main tubular body of a biocompatible graft material, the main tubular body comprising a main lumen, a distal end and a proximal end; and
an elongate tubular bridge of a biocompatible graft material, the elongate tubular bridge extending around a portion of the main tubular body and forming a bridging lumen bridging between two circumferentially spaced-apart openings within the main tubular body, the tubular bridge comprising at least two fenestrations.

In one embodiment, the tubular bridge comprises concertinaed graft material.

In one embodiment, the concertinaed graft material comprises a plurality of circumferential crimps.

In one embodiment, a first sub-set of the circumferential crimps project outwards radially.

In one embodiment, a second sub-set of the circumferential crimps project inwards radially.

In one embodiment, the tubular bridge comprises at least three fenestrations.

In one embodiment, the tubular bridge comprises first and second end portions joined by an intermediate portion, the first and second end portions located within the main tubular body.

In one embodiment, the first end portion terminates in an opening, the opening comprising a reinforcing end ring.

In one embodiment, the reinforcing end ring is attached to the graft material of the main tubular body.

In one embodiment, the reinforcing end ring is D-shaped.

In one embodiment, the D-shaped reinforcing end ring comprises a relatively straight portion joining ends of a C-shaped portion,
wherein the relatively straight portion is attached to the graft material of the main tubular body such that the relatively straight portion closely follows a portion of the circumference of the main tubular body.

In one embodiment, the first end portion comprises a first longitudinal support wire.

In one embodiment, the second end portion comprises a second longitudinal support wire.

In one embodiment, the stent graft further comprises a plurality of self-expanding Z-stents disposed around the main tubular body.

According to a second aspect of the invention, there is provided a stent graft assembly comprising:
an elongate main tubular body of a biocompatible graft material, the main tubular body comprising a main lumen, a distal end and a proximal end;
an elongate tubular bridge of a biocompatible graft material, the elongate tubular bridge extending around a portion of the main tubular body and forming a bridging lumen bridging between two circumferentially spaced-apart openings within the main tubular body, the tubular bridge comprising at least two fenestrations; and
a peripheral stent graft, the peripheral stent graft having a first portion within the tubular bridge and a second portion extending from one of the at least two fenestrations,
whereby the first portion forms a blood flow barrier within the tubular bridge.

In one embodiment, the tubular bridge comprises concertinaed graft material.

In one embodiment, the concertinaed graft material comprises a plurality of circumferential crimps.

In one embodiment, a first sub-set of the circumferential crimps project outwards radially.

In one embodiment, a second sub-set of the circumferential crimps project inwards radially.

In one embodiment, the tubular bridge comprises at least three fenestrations.

BRIEF DESCRIPTION OF DRAWINGS

Embodiments of the present invention will be discussed with reference to the accompanying drawings wherein:

FIGS. 8 and 9 show an alternative stent graft according to the invention in front and top isometric views respectively;

FIG. 10 shows a component of the stent graft of FIGS. 8 and 9; and

FIG. 11 shows reinforcing wires shown in FIG. 6.

DESCRIPTION OF EMBODIMENTS

Figure 1:
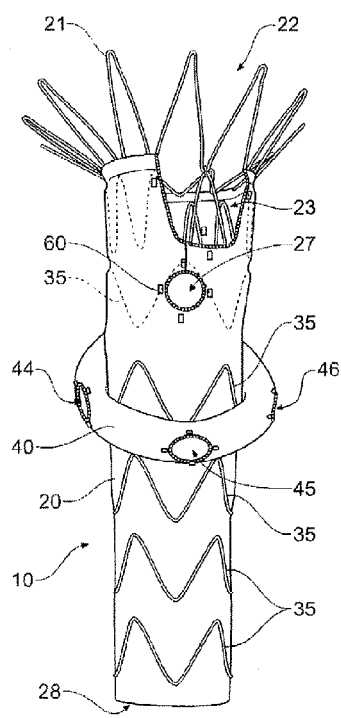
FIGS. 1, 2 and 3, show a stent graft in a front (or anterior), rear (or posterior) and side view respectively.
Figure 2:
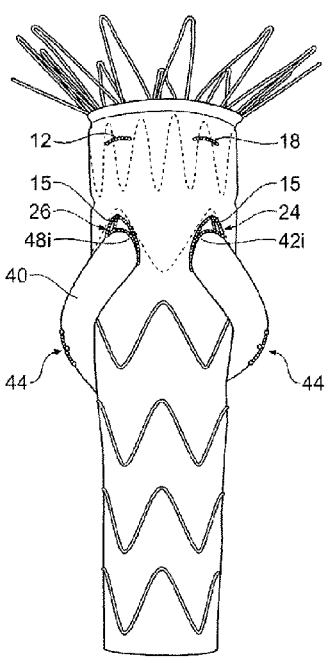

Referring to FIG. 1, there is shown a stent graft 10. The stent graft 10 comprises an elongate main tubular body 20 of a bio-compatible graft material. The main tubular body 20 comprises a distal end 28 and a proximal end 22. The stent graft 10 further comprises an elongate tubular bridge 40 of a bio-compatible graft material. The elongate tubular bridge 40 extends around a portion of the main tubular body 20 and forms a bridging lumen bridging between two circumferentially spaced apart openings 24,26 within the main tubular body 20. The openings 24,26 are shown in FIG. 2. The tubular bridge 40 has three fenestrations 44, 45 and 46. In other embodiments of the invention, more or less fenestrations may be provided. For instance, two, four or even five fenestrations may be appropriate for some applications.

The bio-compatible graft material used for the elongate main tubular body 20 and the elongate tubular bridge 40 can include polytetrafluoroethylene, Dacron, polyamide or any other suitable bio-compatible graft material. Naturally occurring bio-material, such as collagen, particularly a specially derived collagen material known as an extracellular matrix (ECM), such as small intestine submucosa (SIS), may be used.

The tubular body 20 is supported by a plurality of self-expanding stents 35, which are mounted either inside or outside the tubular body. The stents may be constructed from stainless steel, Nitinol (a nickel titanium alloy) or any other suitable material. Each of the stents is a self-expanding Gianturco Z-stent.

The tubular bridge 40 comprises concertinaed graft material. This is most clearly shown in FIGS. 6 and 7A. The concertinaed graft material comprises a plurality of circumferential crimps. Referring to FIG. 7A, it can be seen that these circumferential crimps include a first sub-set 78 of circumferential crimps that project outwards radially and a second sub-set 72 of circumferential crimps that project inwards radially.

Figure 3:
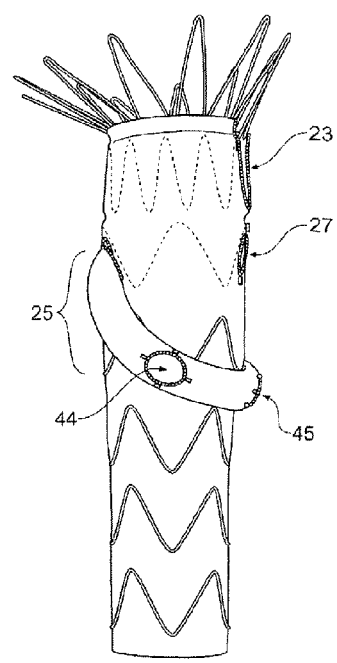

Referring to FIGS. 1, 2 and 3, the stent graft 10 is shown in a front or anterior view in FIG. 1, a posterior or rear view in FIG. 2 and a side view in FIG. 3. In FIG. 1, it can be seen that the stent graft 10 includes a scallop cut out 23 at the proximal end 22. This cut out is provided for the celiac artery. The tubular bridge 40 that extends around a portion 25 of the main tubular body 20 extends into the main lumen 29 through openings 24 and 26. Stitching 15 is used to secure the tubular bridge 40 to the openings 24 and 26 within the main tubular body 20, as is most clearly shown in FIG. 2.

FIG. 1 and FIG. 3 show a fenestration 27 for allowing fluid access from the main lumen 29 to the superior mesenteric artery (SMA).

Figure 4:
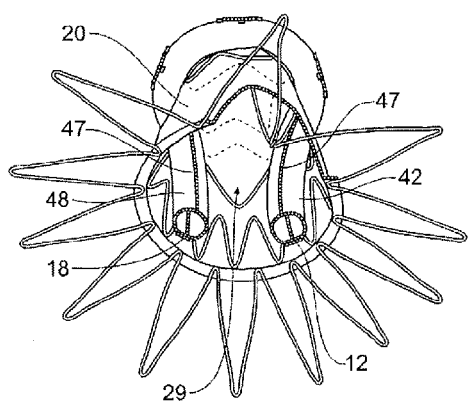
FIG. 4 is an isometric view from above of the stent graft shown in FIGS. 1 to 3.
Figure 6:
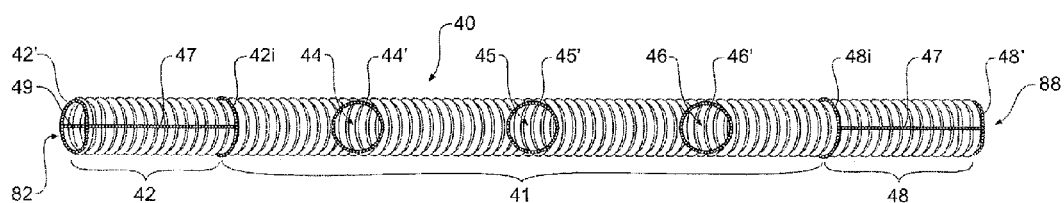
FIG. 6 is an isometric view of a component of the stent graft shown in FIGS. 1 to 4.
Figure 7A:
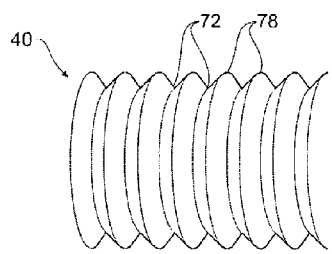
FIG. 7A is a close up view of a portion of the component shown in FIG. 6.

Referring to FIGS. 4 and 6, it can be seen that the tubular bridge 40 includes first and second end portions 42 and 48 joined by an intermediate portion 41. The first and second end portions 42,48 are located within the main tubular body 20, as is clearly shown in FIG. 4.

The construction of the tubular body 40 is shown in more detail in FIG. 6. It can be seen that the end portions 42 and 48 are supported by reinforcing wires. The end portion 42 has a reinforcing ring 42i, a reinforcing end ring 42' and a pair of diametrically opposite longitudinal support wires 47 and 49.

Referring again to FIG. 2, stitching 12 and 15 securing the end ring 42' and the end ring 48' of the tubular bridge 40 is shown.

Referring again to FIG. 6, it can be seen that the first end portion 42 terminates in an opening 82. The opening 82 comprises a reinforcing end ring 42'. In the embodiment of the invention shown in FIGS. 1 through 6, this reinforcing end ring 42' is D-shaped. This is more clearly illustrated in FIG. 11, which shows that the D-shaped reinforcing end ring 42' comprises a relatively straight portion 86 joining ends of a C-shaped portion 84. In contrast, the reinforcing ring 42i, illustrated in FIGS. 6 and 11 is O-shaped, as is most clearly shown in FIG. 11. The relatively straight portion 86 is attached to the graft material of the main tubular body such that the relatively straight portion 86 follows a portion of the circumference of the main tubular body 20. This greatly assists with cannulation. While other embodiments of the invention may include a simple circular reinforcing end ring 42', such an arrangement has a disadvantage where cannulation is required in through the opening 82. This is because a guide wire tracking along an internal surface of the main tubular body 20 will more easily miss the opening 82. With the D-shaped opening, there is a longer portion of the circumference of the main tubular body that effectively forms part of the opening for receiving a guide wire. The reinforcing end rings 42' and 48' may be constructed from stainless steel, Nitinol (a nickel titanium alloy) or any other suitable material.

Figure 7B:
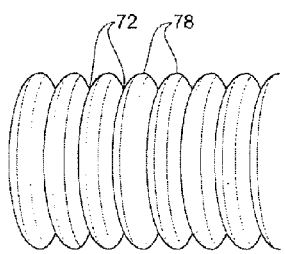
FIGS. 7B and 7C are alternative embodiments for the portion shown in FIG. 7A.
Figure 7C:
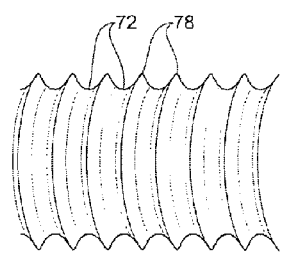

Referring now to FIGS. 7A, 7B and 7C, it can be seen that the tubular bridge 40 comprises concertinaed graft material. The concertinaed graft material comprises a plurality of circumferential crimps. In the embodiment shown in FIG. 7A, there are crimps forming peaks 78 and valleys 72. Alternatively, in the embodiment shown in FIG. 7B, the crimps form valleys 72 and rounded portions between the valleys that project radially outwards. Finally, in the embodiment shown in FIG. 7, crimps form peaks 78 and valleys are formed between the peaks, the valleys extending radially inwards. With all of the embodiments shown in FIGS. 7A, 7B and 7C, the tubular bridge is highly flexible. Not only does the crimping and concertinaing provide flexibility, it may also provide some resistance against radial crashing forces.

Figure 5:
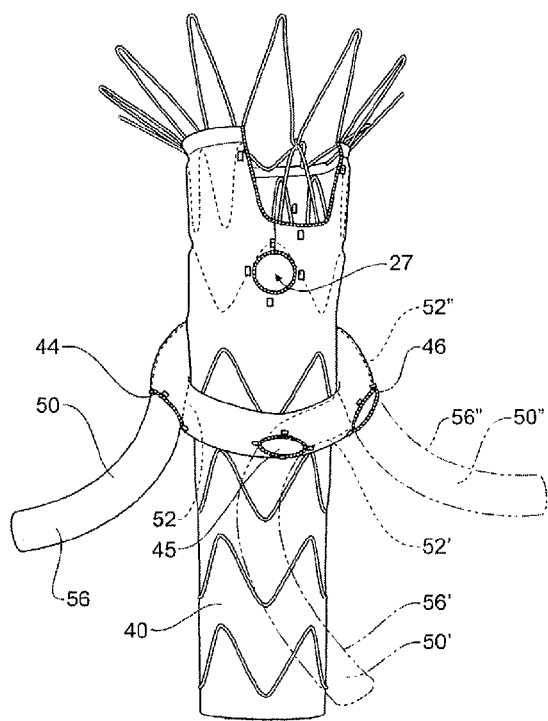
FIG. 5 is a similar view to FIG. 1, but also shows peripheral stent grafts inserted into the stent graft of FIG. 1 so as to form a stent graft assembly.

Turning to FIG. 5, it can be seen that the tubular bridge 50 provides a number of openings 44, 45 and 46 (in this case three) that can be used to feed blood to (perfuse) the renal arteries. In FIG. 5, it can be seen that a peripheral stent graft 50 extends out from within the bridging lumen 40. Shown in dotted outline are the remaining two possible positions for a second peripheral stent graft. The surgeon can choose between the positions shown at 50' and 50" extending from fenestrations 45 and 46 respectively depending on the anatomy of the patient and the position of their renal arteries. Thus, the tubular bridge 40 has an inherent degree of flexibility by virtue of having three or more fenestrations 44, 45 and 46 for the two renal arteries. In addition, the shape, positioning and construction of the tubular bridge 40 all assist in enhancing its mobility so that the fenestrations 44, 45 or 46 can be positioned in close alignment to the renal arteries, thereby facilitating the perfusion into them through, for instance, peripheral stent grafts 50 and 50' (or 50"), as shown in FIG. 5.

Referring now to FIGS. 8, 9 and 10, an alternative embodiment of the invention is shown. With this embodiment of the invention, the tubular bridge 40 does not extend into the main lumen 29. The construction of the tubular bridge 40 is also different, as can be seen in FIG. 10. The end portions 42 and 48 of the first embodiment shown in FIG. 6 are not required. Instead, reinforcing rings 42i and 48i form the ends of the tubular bridge 40. These ends are secured directly onto the main tubular body 20 with stitching 15, as is shown in FIG. 8. One advantage of this embodiment of the invention is that it assists with packaging, as there is less material to be compressed into a delivery device.

Each of the embodiments of the invention described above with reference to the drawings provides a highly adaptable fenestrated stent graft 10 for use in treating infa-renal abdominal aortic aneurisms (AAAs). The stent grafts of the invention provide a better off-the-shelf fenestrated stent graft and thereby reduce, or in some cases eliminate, the need for custom made stent grafts to suite a patient's particular anatomy.

Cannulation of the renal arteries is assisted by use of embodiments of the invention described above. Referring to FIG. 5, it can be seen that once peripheral stents 50 and 50" are deployed, the central part of the tubular bridge 50 becomes sealed thereby preventing blood flow from the unused fenestration 45. Alternatively, if the peripheral stent 50' is used instead of the peripheral stent 50", then blood flow to the unused fenestration 46 is blocked by the wall of the peripheral stent graft 50'.

As can be seen in FIG. 5, the peripheral stent graft 50 has a first portion 52 within the tubular bridge 40 and a second portion 56 extending from the fenestration 44. The first portion 52 forms a blood flow barrier within the tubular bridge 40. This prevents blood flowing towards the fenestrations 45 and 46. Thus, fenestrations 45 and 46 can only be supplied blood through the other end of the tubular bridge 40.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

What is claimed is:

1. A stent graft comprising:
    an elongate main tubular body of a biocompatible graft material, the main tubular body comprising a main lumen, a distal end and a proximal end; and
    an elongate tubular bridge of a biocompatible graft material and having an inner lumen, the elongate tubular bridge extending around a portion of the main tubular body and forming a bridging lumen bridging between two circumferentially spaced-apart openings within the main tubular body, the tubular bridge comprising at least two fenestrations, wherein the elongate tubular main body does not extend within the lumen.

2. The stent graft as claimed in claim 1 wherein the tubular bridge comprises concertinaed graft material.

3. The stent graft as claimed in claim 2 wherein the concertinaed graft material comprises a plurality of circumferential crimps.

4. The stent graft as claimed in claim 3 wherein a first sub-set of the circumferential crimps project outwards radially.

5. The stent graft as claimed in claim 4 wherein a second sub-set of the circumferential crimps project inwards radially.

6. The stent graft as claimed in claim 2 wherein the tubular bridge comprises at least three fenestrations.

7. The stent graft as claimed in claim 1 wherein the tubular bridge comprises first and second end portions joined by an intermediate portion, the first and second end portions located within the main tubular body.

8. The stent graft as claimed in claim 7 wherein the first end portion terminates in an opening, the opening comprising a reinforcing end ring.

9. The stent graft as claimed in claim 8 wherein the reinforcing end ring is attached to the graft material of the main tubular body.

10. The stent graft as claimed in claim 9 wherein the reinforcing end ring is D-shaped.

11. The stent graft as claimed in claim 10 wherein the D-shaped reinforcing end ring comprises a relatively straight portion joining ends of a C-shaped portion,
    wherein the relatively straight portion is attached to the graft material of the main tubular body such that the relatively straight portion closely follows a portion of the circumference of the main tubular body.

12. A stent graft comprising:
    an elongate main tubular body of a biocompatible graft material, the main tubular body comprising a main lumen, a distal end and a proximal end; and
    an elongate tubular bridge of a biocompatible graft material, the elongate tubular bridge extending around a portion of the main tubular body and forming a bridging lumen bridging between two circumferentially spaced-apart openings within the main tubular body, the tubular bridge comprising at least two fenestrations, wherein the tubular bridge comprises first and second end portions joined by an intermediate portion, the first and second end portions located within the main tubular body, and wherein the first end portion comprises a first longitudinal support wire.

13. The stent graft as claimed in claim 12 wherein the second end portion comprises a second longitudinal support wire.

14. The stent graft as claimed in claim 1 comprising a plurality of self-expanding Z-stents disposed around the main tubular body.

15. A stent graft assembly comprising:
    an elongate main tubular body of a biocompatible graft material, the main tubular body comprising a main lumen, a distal end and a proximal end;
    an elongate tubular bridge of a biocompatible graft material, the elongate tubular bridge extending around a portion of the main tubular body and forming a bridging lumen bridging between two circumferentially spaced-apart openings within the main tubular body, the tubular bridge comprising at least two fenestrations; and a peripheral stent graft, the peripheral stent graft having a first portion within the tubular bridge and a second portion extending from one of the at least two fenestrations, whereby the first portion forms a blood flow barrier within the tubular bridge.

16. The stent graft assembly as claimed in claim 15 wherein the tubular bridge comprises concertinaed graft material.

17. The stent graft assembly as claimed in claim 16 wherein the concertinaed graft material comprises a plurality of circumferential crimps.

18. The stent graft assembly as claimed in claim 17 wherein a first sub-set of the circumferential crimps project outwards radially.

19. The stent graft assembly as claimed in claim 18 wherein a second sub-set of the circumferential crimps project inwards radially.

20. The stent graft assembly as claimed in claim 16 wherein the tubular bridge comprises at least three fenestrations.

21. A stent graft comprising:
- an elongate main tubular body of a biocompatible graft material, the main tubular body comprising a main lumen, a distal end and a proximal end; and
- an elongate tubular bridge of a biocompatible graft material having a first open end, a second open end, and a side wall of graft material between the first and second open ends, the elongate tubular bridge extending around a portion of the main tubular body and forming a bridging lumen bridging between two circumferentially spaced-apart openings within the main tubular body, the tubular bridge comprising at least two fenestrations in the side wall between the first and second open ends.

* * * * *